US012599628B2

(12) United States Patent
Russo et al.

(10) Patent No.: US 12,599,628 B2
(45) **Date of Patent: \*Apr. 14, 2026**

(54) MITIGATION OF CRYPTOSPORIDIOSIS USING HYDROGEN PEROXIDE-GENERATING COMPOSITIONS

(71) Applicant: Purina Animal Nutrition, LLC, Arden Hills, MN (US)

(72) Inventors: Kay Russo, Fort Collins, CO (US); Theodore Karnezos, Colchester, VT (US)

(73) Assignee: Purina Animal Nutrition, LLC, Arden Hills, MI (US)

( \* ) Notice: Subject to any disclaimer, the term of this patent is extended or adjusted under 35 U.S.C. 154(b) by 0 days.

This patent is subject to a terminal disclaimer.

(21) Appl. No.: 19/221,315

(22) Filed: May 28, 2025

(65) Prior Publication Data

US 2025/0288609 A1     Sep. 18, 2025

Related U.S. Application Data

(60) Continuation of application No. 18/763,332, filed on Jul. 3, 2024, now Pat. No. 12,337,013, which is a division of application No. 17/719,674, filed on Apr. 13, 2022, now Pat. No. 12,053,487.

(60) Provisional application No. 63/175,015, filed on Apr. 14, 2021.

(51) Int. Cl.

| | |
|---|---|
| *A23K 10/20* | (2016.01) |
| *A23K 10/14* | (2016.01) |
| *A23K 20/163* | (2016.01) |
| *A23K 20/22* | (2016.01) |
| *A23K 50/10* | (2016.01) |
| *A23K 50/60* | (2016.01) |
| *A61K 31/7004* | (2006.01) |
| *A61K 33/40* | (2006.01) |
| *A61K 38/44* | (2006.01) |
| *A61P 33/02* | (2006.01) |

(52) U.S. Cl.
CPC .............. *A61K 33/40* (2013.01); *A23K 10/14* (2016.05); *A23K 20/163* (2016.05); *A23K 20/22* (2016.05); *A23K 50/10* (2016.05); *A23K 50/60* (2016.05); *A61K 31/7004* (2013.01); *A61K 38/443* (2013.01); *A61P 33/02* (2018.01)

(58) Field of Classification Search
None
See application file for complete search history.

(56) References Cited

U.S. PATENT DOCUMENTS

| | | |
|---|---|---|
| 9,257,461 B2 | 2/2016 | Cho et al. |
| 10,771,669 B1 | 9/2020 | Balasubramanian et al. |
| 2010/0189707 A1 | 7/2010 | Barnett |
| 2011/0229598 A1 | 9/2011 | Musser |
| 2011/0300021 A1 | 12/2011 | Becker et al. |
| 2014/0023597 A1 | 1/2014 | Barrett et al. |
| 2019/0336522 A1 | 11/2019 | Miller et al. |
| 2020/0404177 A1 | 12/2020 | Sapienza et al. |
| 2022/0331356 A1 | 10/2022 | Russo et al. |
| 2024/0350539 A1 | 10/2024 | Russo et al. |

FOREIGN PATENT DOCUMENTS

| | | |
|---|---|---|
| CN | 112422798 A | 2/2021 |
| WO | 03009702 A1 | 2/2003 |
| WO | 2020074672 A2 | 4/2020 |
| WO | 2022221380 A1 | 10/2022 |

OTHER PUBLICATIONS

Office Action issued in Chinese Patent Application No. 202280039226. 5, mailed on Jun. 27, 2025, 20 pages including 12 pages of English translation.
Weir, et al., "Efficacy of Common Laboratory Disinfectants on the Infectivity of Cryptosporidium parvum Oocysts in Cell Culture", Applied and Environmental Microbiology, vol. 68, No. 5, pp. 2576-2579, May 2002, American Society for Microbiology.
International Preliminary Report on Patentability issued in International Application No. PCT/US2022/024569, mailed on Oct. 26, 2023, 8 pages.
International Search Report and Written Opinion issued in International Application No. PCT/US2022/024569, mailed on Aug. 24, 2022, 14 pages.
"Glucose", Wikipedia entry, retrieved on Jun. 9, 2022 from https:/ en.wikipedia.org/w/index.php?title=Glucose&oldid=953651730, 20 pages.
Castro-Hermida, et al., "Evaluation of two Commercial Disinfectants on the Viability and Infectivity of Cryptosproidium parvum Oocysts", The Veterinary Journal, vol. 171, pp. 340-345, 2006, Elsevier Ltd.
Watarai, et al., "Feeding Activated Charcoal from Bark Containing Wood Vinegar Liquid (Nekka-Rich) Is Effective as Treatment for Cryptosporidiosis in Calves", Journal of Dairy Sciences, vol. 91, pp. 1458-1463, 2008, American Dairy Sciences Association.
Yang, Luliang, "Glucose Oxidase (GOX)", 26 pages, Nov. 2019, Beijing Winovazyme.
Office Action issued in Taiwanese Patent Application No. 111114073, issued on Nov. 5, 2025, 8 pages including 4 pages of machine English translation.

(Continued)

*Primary Examiner* — Jennifer E Graser
(74) *Attorney, Agent, or Firm* — Dorsey & Whitney LLP

(57) ABSTRACT

Compositions for preventing or decreasing cryptosporidiosis include sources of hydrogen peroxide and are fed to animals. The animals may be neonatal calves and the cryptosporidiosis may be caused by *Cryptosporidium parvum*. Methods of preventing or decreasing cryptosporidiosis in animals by feeding the hydrogen peroxide-generating compositions to the animals are also disclosed. Some disclosed methods reduce the number of *Cryptosporidium* oocysts shed by an infected animal or reduce the infectivity of *Cryptosporidium oocysts* shed by an infected animal. Some methods include feeding the hydrogen peroxide-generating compositions to animals ultimately afflicted with cryptosporidiosis, and the animals gain weight despite the infection.

19 Claims, 8 Drawing Sheets

(56)         References Cited

OTHER PUBLICATIONS

Technical Examination Report issued in Brazilian Application No. 122025007253-2, mailed on Oct. 31, 2025, 14 pages including 7 pages of machine English translation.

MITIGATION OF CRYPTOSPORIDIOSIS USING HYDROGEN PEROXIDE-GENERATING COMPOSITIONS

CROSS-REFERENCE TO RELATED APPLICATION

This application is a continuation of U.S. application Ser. No. 18/763,332, filed on Jul. 3, 2024, issued as U.S. Pat. No. 12,337,013 on Jun. 24, 2025, entitled "MITIGATION OF CRYPTOSPORIDIOSIS USING HYDROGEN PEROX-IDE-GENERATING COMPOSITIONS", which in turn is a divisional of U.S. application Ser. No. 17/719,674, filed on Apr. 13, 2022, issued as U.S. Pat. No. 12,053,487 on Aug. 6, 2024, entitled "Mitigation of Cryptosporidiosis Using Hydrogen Peroxide-Generating Compositions", which in turn claims priority to U.S. Provisional Patent Application No. 63/175,015, filed Apr. 14, 2021, entitled "Mitigation of Cryptosporidiosis Using Hydrogen Peroxide-Generating Compositions", which is hereby incorporated by reference in its entirety for all purposes.

TECHNICAL FIELD

The present disclosure relates to compositions and methods for mitigating cryptosporidiosis, or reducing the number and/or infectivity of *Cryptosporidium* oocysts.

BACKGROUND

Cryptosporidiosis is a diarrheal disease caused by the zoonotic protozoan parasites *Cryptosporidium* spp., which are prevalent in the United States and worldwide. Young animals are often more susceptible than are adults. *Cryptosporidium* oocysts are shed in the feces of infected animals and are spread through ingestion of contaminated water, food, or other materials. The oocysts are durable, including being resistant to chlorine disinfectant, and can thereby transfer readily between animals in confined or shared spaces, such as dairy or beef calves. Currently, there are no approved therapeutics in the United States for combatting *Cryptosporidium* infection in food animals. Reducing the number of oocysts shed by an infected animal and/or reducing the infectivity of shed oocysts may help reduce transmission or severity of cryptosporidiosis.

SUMMARY

The present disclosure includes compositions and methods for mitigating cryptosporidiosis, or reducing the number and/or infectivity of *Cryptosporidium* oocysts. The compositions include a hydrogen peroxide-generating source, which may be sodium percarbonate or glucose oxidase with dextrose. The compositions can be added to animal feed, which may be milk replacer if the feed is provided to calves. As illustrated herein, the compositions and methods may reduce the number of oocysts shed from an infected animal and/or reduce the infectivity of the shed oocysts. Animals who are provided the disclosed compositions may gain weight even if infected with *Cryptosporidium*.

In accordance with some embodiments, a method of reducing *Cryptosporidium* spp. in a liquid animal feed involves providing a liquid animal feed admixed with a hydrogen peroxide-generating composition. The composition includes sodium percarbonate or glucose oxidase with dextrose as a source of hydrogen peroxide. The source is provided at about 0.07 wt % to about 3.00 wt % of the liquid animal feed on a dry basis. In some embodiments, the source of hydrogen peroxide is sodium percarbonate and it is provided at about 0.07 wt % to about 0.88 wt % on a dry basis. In some embodiments, the source of hydrogen peroxide is glucose oxidase with dextrose, the glucose oxidase (10,000 U/g) is provided at about 0.01 wt % to about 0.07 wt %, and the dextrose is provided at about 0.31 wt % to about 2.94 wt % on a dry basis. In some embodiments, the liquid animal feed includes whole milk, milk replacer, waste milk, or an electrolyte solution.

In some embodiments, the liquid animal feed is fed to a domestic livestock animal, which prevents or reduces cryptosporidiosis in the animal if the animal is exposed to *Cryptosporidium* spp. The animal may be a calf, lamb, goat kid, piglet, or foal. If the animal is a calf, the *Cryptosporidium* species may be *C. parvum*. In embodiments, the composition is first fed to the animal within 12 to 24 hours of birth, and then fed twice per day for 10 days. In embodiments, an animal that both ingests the composition and is exposed to *Cryptosporidium* spp. improves performance compared to an animal exposed to *Cryptosporidium* spp. but not provided the composition. The improved performance can include improved weight gain.

In accordance with some embodiments, a method of reducing the infectivity of *Cryptosporidium* oocysts excreted by an animal includes providing a source of hydrogen peroxide to an animal before or after infection with *Cryptosporidium* spp. The ability of at least a portion of the *Cryptosporidium* oocysts excreted by the animal to infect a second animal is reduced compared to *Cryptosporidium* oocysts excreted by an animal not provided the source of hydrogen peroxide.

In embodiments, the animal is a calf, lamb, goat kid, piglet, and foal. In embodiments, the source of hydrogen peroxide is sodium percarbonate or glucose oxidase with dextrose. In embodiments, the source of hydrogen peroxide is sodium percarbonate, and it is provided at 750 mg/head/day to 3000 mg/head/day. In embodiments, the source of hydrogen peroxide is glucose oxidase with dextrose, the glucose oxidase (10,000 U/g) is provided at 140 mg/head/day to 250 mg/head/day, and the dextrose is provided at 3.5 g/head/day to 10.0 g/head/day.

In embodiments, the source of hydrogen peroxide is provided in water, whole milk, milk replacer, waste milk, or an electrolyte solution. In embodiments, the source of hydrogen peroxide is encapsulated. In embodiments, the animal is a calf and the *Cryptosporidium* species is *C. parvum*. In response to ingesting the source of hydrogen peroxide, the animal may shed fewer oocysts compared to an animal not provided the source of hydrogen peroxide.

In accordance with some embodiments, a method of feeding a calf susceptible to infection with *Cryptosporidium parvum* includes providing a liquid feed—which includes whole milk, milk replacer, or waste milk, and a hydrogen peroxide-generating composition—to the calf, and the calf gains weight compared to a calf not provided the composition. In embodiments, the calf susceptible to infection with *C. parvum* and the calf not provided the composition are both infected with *C. parvum*.

In embodiments, the hydrogen peroxide-generating composition is sodium percarbonate or glucose oxidase with dextrose. In embodiments, the hydrogen peroxide-generating composition is sodium percarbonate, and it is provided at 750 mg/head/day to 3000 mg/head/day. In embodiments, the hydrogen peroxide-generating composition is glucose oxidase with dextrose, the glucose oxidase (10,000 U/g) is provided at 140 mg/head/day to 250 mg/head/day, and the dextrose is provided at 3.5 g/head/day to 10.0 g/head/day. In embodiments, the composition is first provided within 12 to 24 hours of birth, and then provided twice per day for 10 days. In embodiments, the milk replacer includes about 18 wt % to about 30 wt % protein and about 15 wt % to about 30 wt % fat by dry weight.

DETAILED DESCRIPTION

Figure 1:
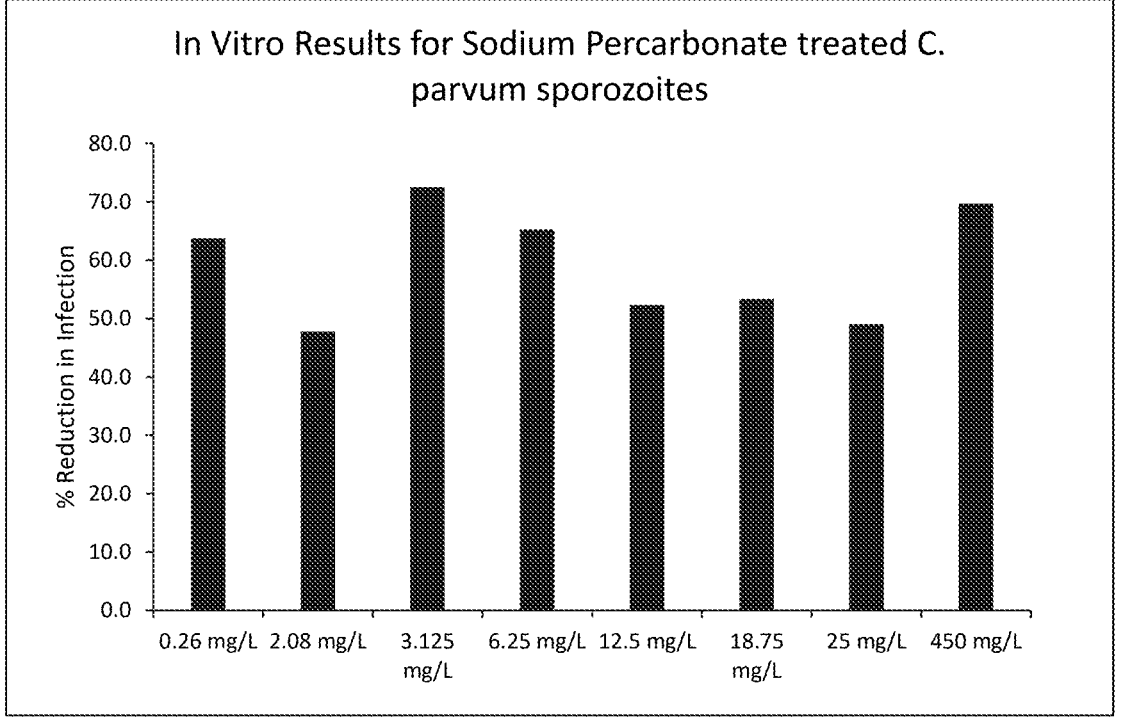
FIG. 1 is a bar graph showing the percent reduction in infection by *C. parvum* sporozoites of HCT-8 cells treated with sodium percarbonate compared to an untreated control.

The present disclosure provides hydrogen peroxide-generating compositions as mitigants and methods of feeding the same to livestock animals to prevent or decrease cryptosporidiosis, or reduce the number or infectivity of shed *Cryptosporidium* oocysts. In embodiments, the hydrogen peroxide-generating compositions include a source of hydrogen peroxide. The source of hydrogen peroxide may be sodium percarbonate or glucose oxidase plus dextrose. In embodiments, methods of feeding livestock animals, which may be calves, include providing the mitigant compositions directly to animals, or first adding the mitigant compositions to a liquid feed, such as a milk replacer, or a dry feed, such as calf starter feed. The mitigant compositions may be provided beginning immediately or soon after birth, such as within 12 to 24 hours of birth, and may be provided once or twice per day for about 10 days. Providing the mitigant compositions to a livestock animal according the methods described herein may prevent infection by *Cryptosporidium* spp., which may be *C. parvum*. In an animal infected with *C. parvum*, the mitigant compositions may decrease or eliminate cryptosporidiosis. In some examples, the compositions and methods may reduce the number of *C. parvum* oocysts shed by an infected animal compared to an infected but untreated animal (Example 3). The oocysts shed by an infected, treated animal may be less infective than oocysts shed by an infected, untreated animal (Example 4). Infected, treated animals may gain weight compared to infected, untreated animals (Example 3).

As used herein, unless the context suggests otherwise, the term "decreasing" includes ameliorating at least one symptom of cryptosporidiosis, reducing the duration or severity of cryptosporidiosis, reducing the number of *Cryptosporidium* oocysts shed by an infected animal, and/or reducing the infectivity of *Cryptosporidium* oocysts shed by an animal. The term "preventing" includes complete prevention of cryptosporidiosis or reducing the risk of *Cryptosporidium* infection. Cryptosporidiosis may be "prevented" in an untreated animal that consumes oocysts shed from a treated animal.

Compositions

Compositions disclosed herein include sources of hydrogen peroxide. In some embodiments, the source is a hydrogen peroxide-generating compound. In some embodiments, the source is a hydrogen peroxide-generating enzymatic system. Examples of hydrogen peroxide-generating compounds include sodium percarbonate, sodium perborate, and urea hydrogen peroxide. In one embodiment, the hydrogen peroxide-generating compound is sodium percarbonate. Examples of hydrogen peroxide-generating enzymatic systems include oxidases and their respective substrates. Examples of oxidases include glucose oxidase, sorbitol oxidase, hexose oxidase, choline oxidase, alcohol oxidase, glycerol oxidase, cholesterol oxidase, pyranose oxidase, carboxyalcohol oxidase, L-amino acid oxidase, glycine oxidase, pyruvate oxidase, glutamate oxidase, sarcosine oxidase, lysine oxidase, lactate oxidase, vanillyl oxidase, glycolate oxidase, galactose oxidase, uricase, oxalate oxidase, and xanthine oxidase. In one embodiment, the hydrogen peroxide-generating enzymatic system includes glucose oxidase and its substrate, $\beta$-d-glucose (dextrose). The glucose oxidase oxidizes dextrose to gluconolactone and hydrogen peroxide. In some implementations glucose oxidase and dextrose may be effective to produce hydrogen peroxide and the compositions may be free of added oxidizable agents, such as added halides (e.g., iodide) or thiocyanate.

In some embodiments, the hydrogen peroxide-generating compositions are combined with a liquid or solid suitable for feeding to a livestock animal. Examples of liquids to which the compositions may be added include water, whole milk, milk replacer, waste milk, and an electrolyte solution. A starter feed is an example of a solid or dry feed to which the compositions may be added. The compositions may be mixed with a liquid before being mixed with a dry feed. Hydrogen peroxide generation may occur before, after, or both before and after being combined with a feed.

Milk replacers to which the presently disclosed hydrogen peroxide-generating compositions may be added may be produced according to traditional methods in which the fat and protein components of milk replacers are spray dried and combined into a milk replacer powder comprised of soluble or at least suspendable ingredients. Spray drying processes generally involve maintaining a spray dryer at temperatures between 100° C. to 200° C. so that the spray dried component rapidly heats and loses moisture.

The milk replacer can be milk and/or vegetable based, and the nutrient profile generally includes fat and protein. The fat content may range from about 2.25 to about 4.7 wt % of the hydrated milk replacer or from about 8 to about 31 wt % of the milk replacer powder. The level of fat may be tailored for a target animal, e.g., calves, as well as the age of the animals fed. In some examples, a calf milk replacer may include a crude fat content ranging from about 10 to about 20 wt % of the powder or about 3 to about 3.75 wt % of the hydrated milk replacer, and full potential calf milk replacers may include fat from about 25 to about 31 wt % of the powder or about 3.75 to about 4.7 wt % of the hydrated milk replacer. In some embodiments, the powdered milk replacer may have a crude fat content of about 8 to about 12 wt %, about 9 to about 11 wt %, about 10 wt %, about 14 to about 20 wt %, about 16 to about 18 wt %, or about 17 wt %.

Predominant fat sources may be lard, tallow, palm kernel, canola oil or coconut oils, alone or in combination, which may contain various amounts of medium chain triglycerides. In addition, some fat from lecithin and residual fat (e.g., butter fat, milkfat, or both) may contribute to the fat content in milk replacers.

Protein in milk replacers typically ranges from about 2.2 to about 5.1 wt % of the hydrated milk replacer or about 18 to about 30 wt % of the powder. For traditional calf milk replacers, the protein content may be about 22 wt % of the powder or about 3.3 wt % of the rehydrated milk replacer, and milk replacers formulated for enhanced performance, such as full potential milk replacers, may include protein at about 25 to about 28 wt % of the powder or about 3.9 wt % to about 4.8 wt % of the rehydrated milk replacer.

Protein may be sourced from animal (e.g., milk, plasma, egg, and red blood cells) and vegetable sources and combinations thereof. Milk-derived protein sources are generally referred to as milk proteins and may include whey, whey protein concentrate, casein, skim milk, sodium caseinate, and calcium caseinate. Non-milk proteins (NMPs), such as vegetable protein (e.g., soy protein, hydrolyzed soy protein, hydrolyzed soy protein modified, soy protein isolate, wheat concentrates, wheat isolates, pea concentrates, pea isolates, and/or potato proteins), animal protein (e.g., plasma such as bovine or porcine plasma, egg and red blood cells), and single cell protein, alone or in combination, may be included as a protein source in the milk replacer. Non-milk proteins may contain varying levels of phosphorous. For instance, phosphorous may be present at about 0.65 wt % of soybean meal, at about 0.78 wt % of soy protein isolate, at about 0.68 wt % of hydrolyzed soy protein modified, at about 1.0 wt % of dehulled canola meal, and each of these components may be present in NMP-containing milk replacers. NMPs may account for up to from 1 to about 65%, from about 50 to about 65%, about 55 to 65%, about 55 to 60%, or up to or at about 60 or about 65% of the total protein content, with the balance of protein derived from milk protein; while milk protein may account for about 35 to 99%, about 35 to about 50%, about 35 to 45%, about 40 to 45%, up to about 40%, or up to about 35% of the total protein content in the milk replacer in some examples.

Waste milk to which the presently disclosed hydrogen peroxide-generating compositions may be added may be non-saleable transition milk, mastitic milk, or non-saleable antibiotic-treated milk, i.e. milk from antibiotic-treated animals, high somatic cell count milk that a producer has opted not to sell, or milk that is for any reason set aside to be fed to animals rather than sold for human consumption. The waste milk may or may not be pasteurized.

Electrolytes to which the presently disclosed hydrogen peroxide-generating compositions may be added may include one or more of sodium, which may be present at about 70 to about 145 mmol/L; glucose, which may be present at up to about 200 mmol/L; amino acids, such as glycine, which may be present at up to about 145 mmol/L; and an alkalizing agent, which may be acetate, propionate, bicarbonate, citrate, lactate, or a combination thereof, which may be present at about 50 to about 80 mmol/L.

In some implementations, the hydrogen peroxide-generating compositions are combined with dry feed such as starter feed. Starter feeds generally include protein sources at about 18 to about 22 weight percent of the total weight of the feed. In some implementations, the starter feed may include a mixture of one or more of corn, soybean meal, wheat middlings, oats, molasses, fat, ground cotton seed hulls, distillers grains, calcium carbonate, salt, and macronutrients and micronutrients. The starter feed may include about 45 to 50 percent coarse ingredients (e.g., corn, soy, and oats); about 20 percent protein; about 2 to 3 percent fat; about 5 to 6 percent fiber (determined on a NIR basis); about 7 percent acid detergent fiber; about 6 percent molasses; and the balance including a mixture of other nutrients.

Sodium percarbonate may be in the form of a stable powder that remains non-reactive in dry form, which may make it amenable to admixing with dry milk replacer compositions according to the methods described herein. Pure hydrogen peroxide, by contrast, may not be as stable in powder form. In some implementations, sodium percarbonate yields about 27.5% hydrogen peroxide when rehydrated.

In some embodiments, the hydrogen peroxide-generating compositions may be protected such that hydrogen peroxide production does not begin, or production is reduced, until a desired time or location. For example, the hydrogen peroxide-generating composition may be encapsulated or coated to prevent, delay, or control hydrogen peroxide generation. Encapsulation may protect the hydrogen peroxide-generating composition from early degradation in the rumen of animals fed the composition. An encapsulant may be pH-activated such that the encapsulant is formulated to decompose and release the hydrogen peroxide, or the hydrogen peroxide source, in an environment having a specific pH, e.g., the small intestine or cecum of an animal. Encapsulation, which may be achieved by various techniques including but not limited to spray-coating, may result in increased absorption of hydrogen peroxide into the bloodstream via the small intestine, which may increase the effectiveness of hydrogen peroxide at preventing or decreasing cryptosporidiosis. In some embodiments, the encapsulant comprises at least one microbial cell wall-based component. Additionally or alternatively, the encapsulant may contain one or more fat- or wax-based components, e.g., fatty acid glycerides, formulated to protect the hydrogen peroxide-generating compositions from degradation in the rumen, thereby preserving the hydrogen peroxide for intestinal absorption. Acceptable examples of fat-based encapsulants are described in U.S. Pat. No. 9,986,749 to Boucher et al., the entire contents of which are incorporated by reference herein. In some examples, the encapsulant may comprise lipid-based nanoparticles (about 200-500 nm in diameter) formulated to bypass the rumen and release the hydrogen peroxide downstream, e.g., in the intestines.

In some implementations, the disclosed compositions may be free of additives, such as the added oxidizable agents disclosed herein. By comparison, U.S. Application Publication No. 2011/0229598 ("'598 publication") discloses a lactoperoxidase ("LP") system that is activated by the addition of a hydrogen peroxide source and an additional oxidizable agent, such as a halide (e.g., iodide) or isothiocyanate, to milk to inactivate bacterial pathogens in the milk. In the '598 publication, the hydrogen peroxide source may be glucose oxidase, which is present at a maximum of 0.1 g/L. In the presently disclosed compositions and methods, glucose oxidase may be provided at 0.09 g/pint, or 0.189 g/L (see, e.g., Example 3), which is greater than the maximum amount disclosed in the '598 publication.

In some implementations, the disclosed compositions may be free of perhydrolase enzyme and an ester substrate. The presently disclosed compositions and methods may be free of peracid solutions. By comparison, U.S. Application Publication No. 2010/0189707 ("'707 publication") discloses compositions comprising a perhydrolase enzyme, a hydrogen peroxide source, and an ester substrate that generate aqueous peracid solutions, which can be used as disinfectants.

In some implementations, the disclosed compositions are added to a milk replacer, and the milk replacer is free of added acid. By comparison, U.S. Application Publication No. 2019/0336522 ("'522 publication") discloses methods of feeding livestock animals a milk replacer comprising percarbonate, which may be sodium percarbonate, and an acid. The treated milk replacer may reduce *Salmonella* contamination, but no mention is made of *Cryptosporidium* or of cryptosporidiosis.

In view of the art, it is unexpected that the presently disclosed compositions and methods may prevent or decrease cryptosporidiosis, and/or may reduce the number and/or infectivity of *Cryptosporidium* oocysts shed from an infected animal. It is also unexpected that *Cryptosporidium*-infected animals fed the disclosed compositions gained weight.

The compositions disclosed herein may prevent or decrease cryptosporidiosis in livestock animals to which the compositions are administered. The compositions disclosed herein may prevent or reduce the severity of cryptosporidiosis in animals to which the compositions are not directly administered. For example, the compositions may reduce the number of *Cryptosporidium* spp., such as *C. parvum,* oocysts shed by an infected animal to which the compositions have been administered. The reduction in shed oocysts may reduce the likelihood that animals, including those not administered the compositions, will ingest oocysts and themselves become infected. The disclosed compositions may reduce the infectivity of oocysts that are shed by an infected animal to which the compositions have been administered. The reduction in infectivity may reduce the likelihood that animals, including those not administered the compositions, who ingest the oocysts will themselves become infected. In this way, the compositions may help slow or stop transmission of *Cryptosporidium* spp. in a population of animals, including when only a subpopulation of animals ingests the compositions.

Methods of Providing Compositions to Animals

The compositions disclosed herein may be provided to any animal susceptible to *Cryptosporidium* spp. infection. Susceptible animals may include domestic livestock such as cattle, sheep, goats, pigs, and horses. Young animals may be more susceptible to infection than older or adult animals. Susceptible young animals may include calves, lambs, goat kids, piglets, and foals. In some implementations, the compositions are provided prophylactically, such as prior to exposure to *Cryptosporidium* spp. or concurrently with a likely *Cryptosporidium* exposure. In some implementations, the compositions are provided therapeutically, after a known or suspected *Cryptosporidium* exposure.

In some implementations, the hydrogen peroxide-generating compositions are provided beginning immediately or soon after birth, such as within 12 to 24 hours of birth. In some implementations, the compositions are provided for about 6 to about 12 days, or about 8 to about 10 days, or about 10 days. The compositions may be provided once a day or more than once a day, such as twice a day. The compositions may generate hydrogen peroxide before, after, or both before and after being provided to an animal.

In some implementations, the animal may be young livestock mammal and may receive the hydrogen peroxide-generating compositions during one of more of a milk feeding phase, a dry feed phase, and a weaning phase. The milk feeding phase ("MFP") is the period when milk replacer, whole milk, waste milk, or a combination thereof is fed to the young animal. Dry feed may be fed during the MFP, however, the dry feed phase is the time period after the MFP when only dry feed (e.g., starter feed) is fed. Typically, the last week of the MFP is the weaning phase, which is the period when young animals are encouraged to consume only dry feed. The MFP may correspond to the first 42 to 49 days from birth with the weaning phase comprising a portion of this period, described below. The dry feed phase comprised of starter feeding may last from about 42 days to about 84 days from birth.

As set forth above, the milk or milk replacer supplemented with hydrogen peroxide-generating compositions may be offered to the young animal during the MFP or portions thereof (e.g., prior to or during the weaning phase). In some implementations, milk replacer mixed with hydrogen peroxide-generating compositions may be fed at a rate of 1.5 pounds per day (e.g., 0.75 pounds per feeding) on a dry weight basis. This amount may be fed during the MFP, and at a rate of 0.75 pounds per day (e.g., at a single feeding) for example during the weaning phase. In additional or alternative implementations, milk replacer may be provided at about 1.8 pounds per day on a dry weight basis for an initial time period of the MFP lasting about 7 days, about 2.5 pounds per day on a dry weight basis for a next time period of the MFP extending from days 8 to 42 thereafter, and about 1.25 pounds per day on a dry weight basis for a further time period extending from days 43 to 49, such as during the weaning phase. During all or a portion of the time the animal receives milk replacer, the animals may be offered dry feed.

During the weaning phase, e.g., during the last several days of the milk feeding phase, hydrogen peroxide-generating compositions may be provided in the feed provided to the young livestock animal. The weaning phase may be about 7 days long, about 14 days long, between about 7 and about 14 days, or for any integer-bounded time range falling between 1 day and 14 days in length. For example, during the weaning phase, the animal may ingest hydrogen peroxide-generating compositions in milk or milk replacer at a reduced rate compared to that provided during a first portion of the MFP described above, and the reduced rate may correspond to a reduced level of milk replacer offered to the animal during weaning. For example, the young livestock animal may transition from a diet of liquid feed (e.g., calf milk replacer) to a diet of dry feed (e.g., calf starter) and may receive a single feeding of the liquid feed with added hydrogen peroxide-generating compositions per day, and for instance may be fed 0.75 pounds of the supplemented milk replacer per day. In this example, the animal may ingest the same amount of hydrogen peroxide-generating compositions per feeding of milk replacer as the first time period, but receives only one feeding per day. During the weaning phase, in another example, the animal may ingest hydrogen peroxide-generating compositions in dry feed, alone or in combination with hydrogen peroxide-generating compositions in milk replacer.

In some implementations, the hydrogen peroxide-generating composition, which may be sodium percarbonate, is provided in a liquid animal feed. The sodium percarbonate may be provided at about 0.07 wt % to about 0.88 wt % on a dry basis, about 0.07 wt % to about 0.80 wt %, about 0.07 wt % to about 0.70 wt %, about 0.07 wt % to about 0.60 wt %, about 0.07 wt % to about 0.50 wt %, about 0.07 wt % to about 0.40 wt %, about 0.07 wt % to about 0.30 wt %, about 0.07 wt % to about 0.20 wt %, about 0.20 wt % to about 0.88 wt %, about 0.30 wt % to about 0.88 wt %, about 0.40 wt % to about 0.88 wt %, about 0.50 wt % to about 0.88 wt %, about 0.60 wt % to about 0.88 wt %, or about 0.70 wt % to about 0.88 wt % on a dry basis.

In some implementations, the hydrogen peroxide-generating composition includes glucose oxidase with dextrose, and it is provided in liquid animal feed. The glucose oxidase may be provided at about at about 0.01 wt % to about 0.07 wt % on a dry basis when the glucose oxidase has a concentration of 10,000 U/g, about 0.01 wt % to about 0.06 wt %, about 0.01 wt % to about 0.05 wt %, about 0.01 wt % to about 0.04 wt %, about 0.01 wt % to about 0.03 wt %, about 0.02 wt % to about 0.07 wt %, about 0.03 wt % to about 0.07 wt %, about 0.04 wt % to about 0.07 wt %, or about 0.05 wt % to about 0.07 wt % on a dry basis when the glucose oxidase has a concentration of 10,000 U/g.

The dextrose may be provided in liquid animal feed at about 0.30 wt % to about 3.0 wt % on a dry basis, about 0.30 wt % to about 2.5 wt %, about 0.30 wt % to about 2.0 wt %, about 0.30 wt % to about 1.5 wt %, about 0.30 wt % to about 1.0 wt %, about 0.50 wt % to about 3.0 wt %, about 1.0 wt % to about 3.0 wt %, about 1.5 wt % to about 3.0 wt %, or about 2.0 wt % to about 3.0 wt % on a dry basis.

In some implementations, the hydrogen peroxide-generating composition includes sodium percarbonate. During the MFP, the sodium percarbonate may be fed at about 750 mg/head/day to about 3000 mg/head/day, about 750 mg/head/day to about 2750 mg/head/day, about 750 mg/head/day to about 2500 mg/head/day, about 750 mg/head/day to about 2250 mg/head/day, about 750 mg/head/day to about 2000 mg/head/day, about 750 mg/head/day to about 1750 mg/head/day, about 750 mg/head/day to about 1500 mg/head/day, about 1000 mg/head/day to about 3000 mg/head/day, about 1250 mg/head/day to about 3000 mg/head/day, about 1500 mg/head/day to about 3000 mg/head/day, about 1750 mg/head/day to about 3000 mg/head/day, about 2000 mg/head/day to about 3000 mg/head/day, or about 2250 mg/head/day to about 3000 mg/head/day. In some implementations, the sodium carbonate is fed at 1000 mg/head/day to 2000 mg/head/day. In some implementations, the sodium carbonate is fed at 500 mg per dose, twice a day, or 1000 mg/dose, twice a day. The rate may be reduced during the weaning phase, as described above.

In some implementations, the hydrogen peroxide-generating composition includes glucose oxidase with dextrose. During the MFP, the glucose oxidase may be fed at about 1400 U/head/day to 2400 U/head/day, about 1400 U/head/day to 2200 U/head/day, about 1400 U/head/day to 2000 U/head/day, about 1400 U/head/day to 1800 U/head/day, about 1600 U/head/day to 2400 U/head/day, about 1800 U/head/day to 2400 U/head/day, or about 2000 U/head/day to 2400 U/head/day. In some implementations, the glucose oxidase is fed at 1800 U/head/day. In some implementations, the glucose oxidase is fed at 900 U per dose, twice a day. The rate may be reduced during the weaning phase, as described above.

During the MFP, the glucose oxidase may be fed at about 140 mg/head/day to 250 mg/head/day, about 140 mg/head/day to 225 mg/head/day, about 140 mg/head/day to 200 mg/head/day, about 140 mg/head/day to 175 mg/head/day, about 160 mg/head/day to 250 mg/head/day, about 180 mg/head/day to 250 mg/head/day, or about 200 mg/head/day to 250 mg/head/day. In some implementations, the glucose oxidase is fed at 180 mg/head/day. In some implementations, the glucose oxidase is fed at 90 mg per dose, twice a day. The rate may be reduced during the weaning phase, as described above.

During the MFP, the dextrose may be fed at about 3.5 g/head/day to about 10.0 g/head/day, about 3.5 g/head/day to about 9.5 g/head/day, about 3.5 g/head/day to about 9.0 g/head/day, about 3.5 g/head/day to about 8.5 g/head/day, about 3.5 g/head/day to about 8.0 g/head/day, about 3.5 g/head/day to about 7.5 g/head/day, about 3.5 g/head/day to about 7.0 g/head/day, about 3.5 g/head/day to about 6.5 g/head/day, about 3.5 g/head/day to about 6.0 g/head/day, about 4.0 g/head/day to about 10.0 g/head/day, about 4.5 g/head/day to about 10.0 g/head/day, about 5.0 g/head/day to about 10.0 g/head/day, about 5.5 g/head/day to about 10.0 g/head/day, about 6.0 g/head/day to about 10.0 g/head/day, about 6.5 g/head/day to about 10.0 g/head/day, about 7.0 g/head/day to about 10.0 g/head/day, about 7.5 g/head/day to about 10.0 g/head/day, or about 8.0 g/head/day to about 10.0 g/head/day. In some implementations, the dextrose is fed at 4.6 g/head/day. In some implementations, the glucose oxidase is fed at 2.3 g per dose, twice a day. The rate may be reduced during the weaning phase, as described above.

In some implementations, glucose oxidase is fed at 180 mg/head/day along with dextrose at 4.6 g/head/day. In some implementations, glucose oxidase is fed at 90 mg per dose along with dextrose at 2.3 g per dose, twice a day.

EXAMPLES

Example 1—In Vitro *Cryptosporidium* Exposure

Sodium percarbonate (0.26, 2.08, 3.125, 6.25, 12.5, 18.75, 25, or 450 mg/L) was tested for its ability to neutralize *C. parvum* sporozoites in host epithelial cells.

HCT-8 (human ileocecal adenocarcinoma) cells were grown in a monolayer to 85-90% confluency in RPMI-1640 medium. Freshly excysted, washed *C. parvum* sporozoites were mixed with a sodium percarbonate treatment and then added to HCT-8 cells at $1.25 \times 10^6$ sporozoites per monolayer. The cells were incubated with the sporozoites for 2 hours at 10% $CO_2$, 37° C. Cells were then washed and incubated in fresh media for 22 hours. Infected, untreated cells served as a control. After incubation, infected cells were harvested and DNA was isolated. The number of *C. parvum* were quantified using qPCR for the *Cryptosporidium* oocyst wall protein (COWP) gene.

Results are presented in FIG. 1, which shows that sodium percarbonate at all treatment concentrations significantly reduced infected compared to control (p<0.05). The results demonstrate that sodium percarbonate reduces infection by *C. parvum* sporozoites in HCT-8 cells.

Example 2—Mouse *Cryptosporidium* Challenge

Sodium percarbonate ("NPC") at 0.26 mg/head, 12.5 mg/head, or 450 mg/head was tested in a *Cryptosporidium* challenge in mice. Eight-day-old ICR or CD-1 mice were divided into treatment (UA) and control (water) groups (n=10/group). Mice were infected with $1 \times 10^4$ *C. parvum* oocysts by oral inoculation. At the time of infection, and for every 12 hours thereafter, mice were treated with 100 µl per dose of NPC or water. A total of 8 doses per mouse were administered before termination of the challenge and collection of the intestines. The experiment was repeated twice ("Challenges I and II"). Infection levels were determined by qPCR against a known standard curve of *C. parvum* organisms.

Figure 2:
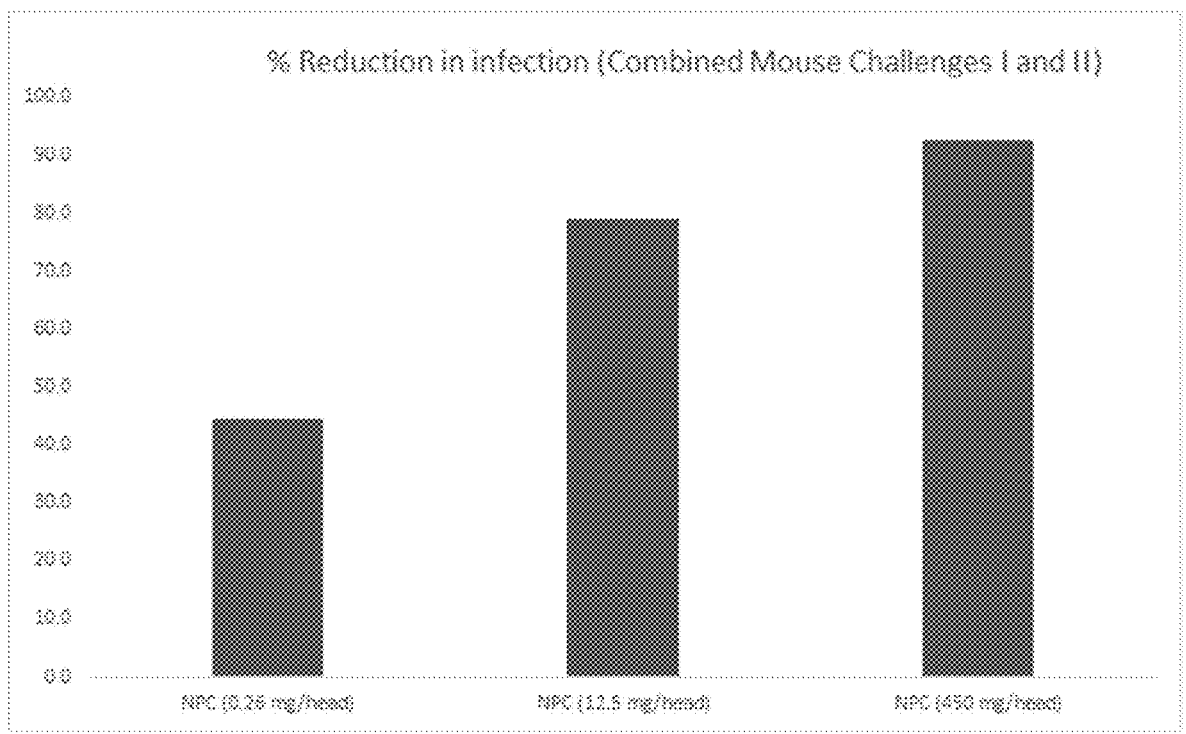
FIG. 2 is a bar graph showing the percent reduction in infection by *C. parvum* sporozoites of mice treated with sodium percarbonate compared to an untreated control.

Results are presented in FIG. 2. For each treatment, percent reduction in *C. parvum* infection increased as treatment dose increased. Sodium percarbonate (450 mg/head) reduced infection from *C. parvum* oocysts by 89.9% compared to control.

Example 3 —Clinical Calf Cryptosporidiosis Trial

The effects of glucose oxidase and sodium percarbonate were studied in a calf model of clinical cryptosporidiosis. Imboden et al., 2012, *Vet. Parasitol.* 188:41-47.

Male Holstein calves were sourced from a closed herd production unit. At birth, calves were protected from exposure to exogenous sources of *Cryptosporidium* spp. and other potential diarrheal agents, including by manually delivering calves onto clean plastic sheeting. Ecolizer® (*Clostridium perfringens* Type C antitoxin and anti-*Escherichia coli* neutralizing antibody, Novartis, Larchwood, IA) and Calfguard® (bovine rotavirus and coronavirus, Zoctis, Kalamazoo, MI) vaccines were administered within two hours of birth. Calves were fed a commercial colostrum replacer at birth per the manufacturer's instructions (Bovine IgG Colostrum Replacement, Land O'Lakes, Shoreview, MN). Adequacy of passive transfer of colostral IgG was determined by using a refractometer to measure serum from each calf collected at 24-36 h of age. Bo-Se® vitamin E/Se supplement (3 ml/45 kg) (Merck, Whitehouse Station, NJ) was injected subcutaneously to each calf within 12 h of birth.

Calves were transported by van in disinfected crates containing autoclaved straw to the University of Arizona BSL2 isolation facility. Upon arrival, calves were weighed and randomly assigned to a treatment group or the control group by blind code using the Microsoft Excel Random Number Generation Tool (4-6 calves total per cohort). Calves were car tagged with an identifying number. Researchers were blinded to calf group assignments. Each calf was housed in a separate elevated calf stall (Wenke Manufacturing, Pender, NE) previously disinfected with ammonia and allowed to air dry for at least 96 hours to inactivate any *Cryptosporidium* or other microbial agents.

Beginning at 12 h of age, calves were maintained on antibiotic-free milk replacer (Land O'Lakes Nursing Formula MOS Milk Replacer, Land O'Lakes Animal Milk Solutions, Arden Hills, MN) twice daily (10% body weight for days 1-5 and thereafter 50% more for trial duration) until termination of the experiment at day 10 post-infection. Potable water (4 L per bucket) was available ad libitum. At the onset of diarrhea, an oral electrolyte solution (Re-Sorb®, Pfizer) was provided by bucket until the end of the trial.

Beginning at 12-24 hours of age, calves were fed sodium percarbonate ("NPC") at 1000 mg ("High" dose) or 500 mg ("Low" dose) or glucose oxidase (90 mg of 10,000 U/g) (Winovazyme)+dextrose (2.3 g) ("GOD") BID in 1 pint milk replacer for the duration of the trial (22 doses total). Control animals received milk replacer without a treatment additive.

Calves were infected at 36-48 hours of age (Day 0) by oral inoculation with $5 \times 10^7$ purified, disinfected *C. parvum* oocysts (Iowa isolate) as previously described. Imboden et al., 2012.

The total volume of feces excreted in a 24-hour period was collected starting on Day 3 post-infection ("PI") and evaluated for diarrhea severity as well as possible bacterial enteropathogens (*E. coli* K99 and *Salmonella*) by standard methods operative in the Arizona Veterinary Diagnostic Laboratory (University of Arizona). Feces were also processed for total daily oocyst counts by real-time PCR. Fecal collection pans were positioned beneath the rear of the stall and were protected from urine contamination by attachment of a urine-diverting full-width angled plastic shield to the underside of the stall floor. Calves were examined twice daily to assess and assign numerical scores for the following variables: clinical symptom, general health observations (willingness to rise, stance, rectal temperature, appetite and food intake, attitude, hydration status), presence or absence of diarrhea, and fecal consistency. Imboden et al., 2012. Calves were reweighed at trial termination to calculate average body weight gain.

Calves were euthanized on Day 10 PI, or before if clinically indicated. Two control calves were euthanized at the start of trial due to congenital defects that had not been detected at birth. One calf each from the Low NPC and GOD group was euthanized on Day 5 and 6 PI, respectively, due to bloat caused by severe diarrhea and possible torsion of gut.

Statistical significance was determined by t-test. No major toxic effects were observed in calves in the treatment groups.

Figure 3:
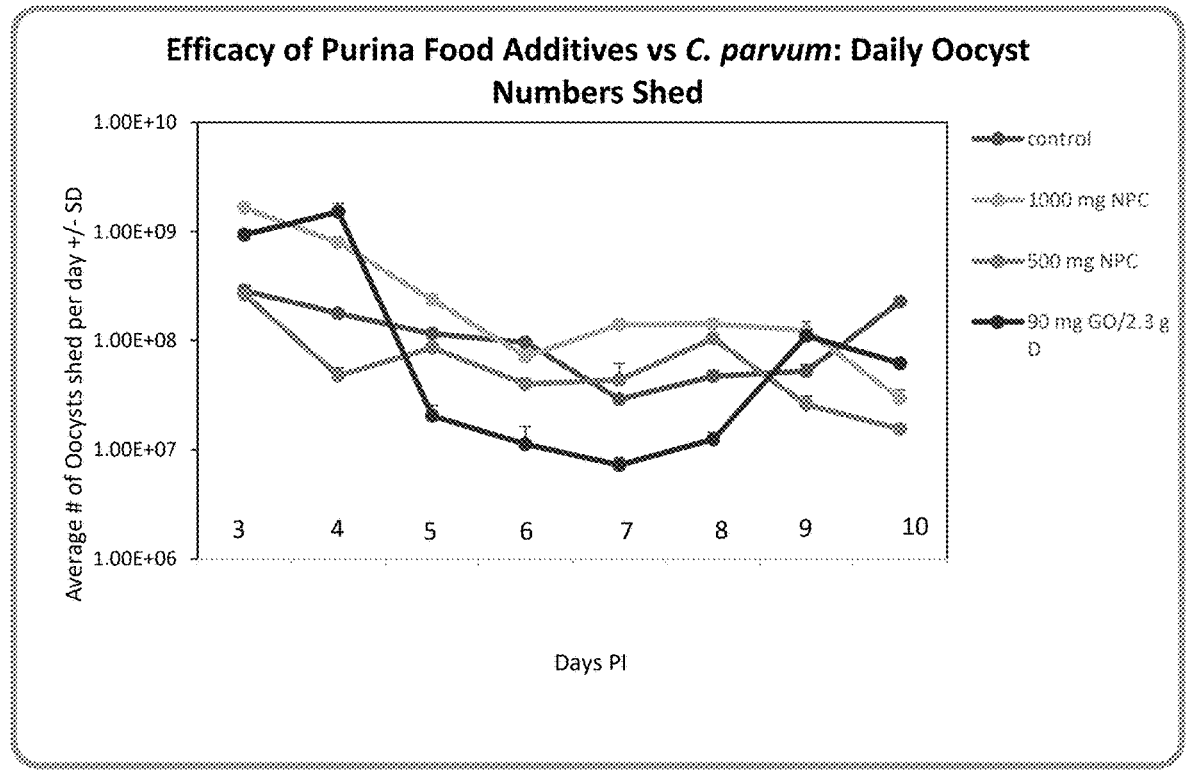
FIG. 3 is a line graph, in logarithmic scale, showing the average number of *C. parvum* oocysts shed by infected calves treated with 1000 mg sodium percarbonate ("NPC"), 500 mg NPC, or 90 mg glucose oxidase ("GO") plus 2.3 g dextrose ("D") BID or untreated ("control").
Figure 4:
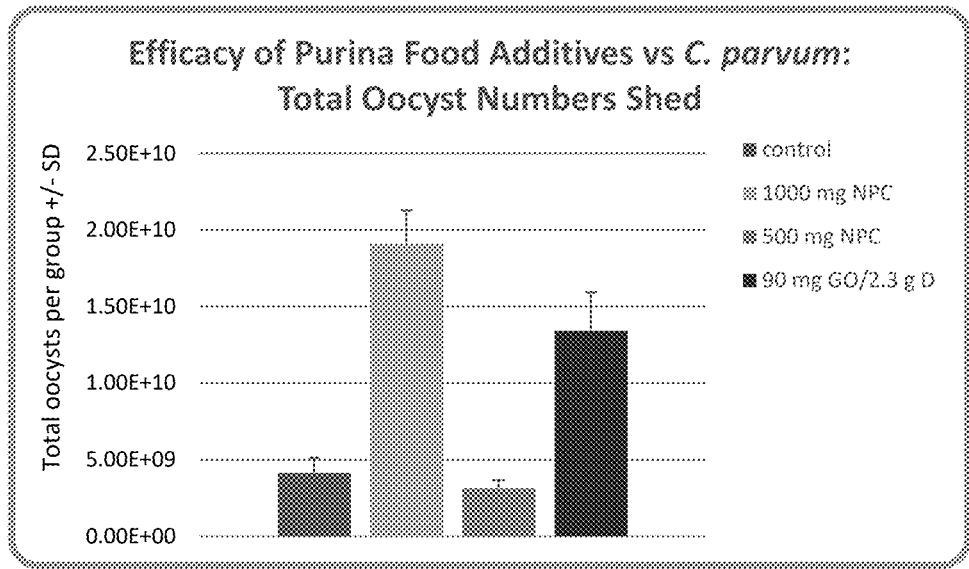
FIG. 4 is a bar graph showing the total number of *C. parvum* oocysts shed by infected control calves or infected calves treated with 1000 mg NPC, 500 mg NPC, or 90 mg GO plus 2.3 g D BID or untreated.

Results are presented in FIGS. 3-7. FIG. 3 demonstrates that the mean daily number of oocysts shed was significantly lower for the treatment groups than the control group. The 1000 mg NPC treatment group shed significantly fewer oocysts on Days 6 and 10 PI compared to the control group (p<0.05). The 500 mg NPC treatment group shed significantly fewer oocysts on Days 4-6 and 9-10 PI compared to the control group (p<0.05). The GOD treatment group shed significantly fewer oocysts on Days 5-8 and 10 PI compared to the control group (p<0.05). FIG. 4 demonstrates that the mean total number of oocysts shed over the duration of the trial (Days 3—10 PI) was significantly reduced, by about 24%, in the 500 mg NPC treatment group compared to the control group (p<0.05).

Figure 5:
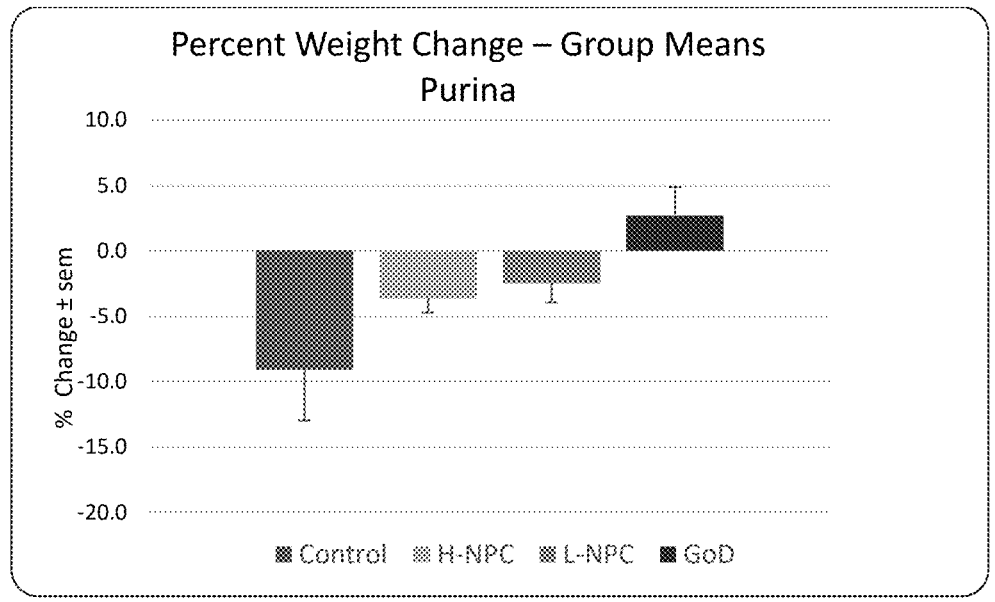
FIG. 5 is a bar graph showing the percent change in body weight of *C. parvum*-infected calves treated with 1000 mg NPC ("H-NPC"), 500 mg NPC ("L-NPC"), or 90 mg GO plus 2.3 g D ("GOD") BID or untreated.

FIG. 5 shows that, over the course of the trial, calves in the GOD treatment group experienced a 2.7% increase in weight, calves in the L-NPC treatment group experienced a 2.5% decrease in weight, calves in the H-NPC treatment group experienced a 3.6% decrease in weight, and calves in the control group experienced a 9.1% decrease in weight. Calves in the GOD treatment group demonstrated statistically significant weight gain compared to the control group (p<0.05). Calves in the control group and in both NPC treatment groups lost weight over the course of the trial, but the calves in the NPC treatment groups tended to lose less weight than did calves in the control group. Weight gain is uncommon and unexpected in challenged treatment groups, even when testing traditional drug therapeutics.

Figure 6:
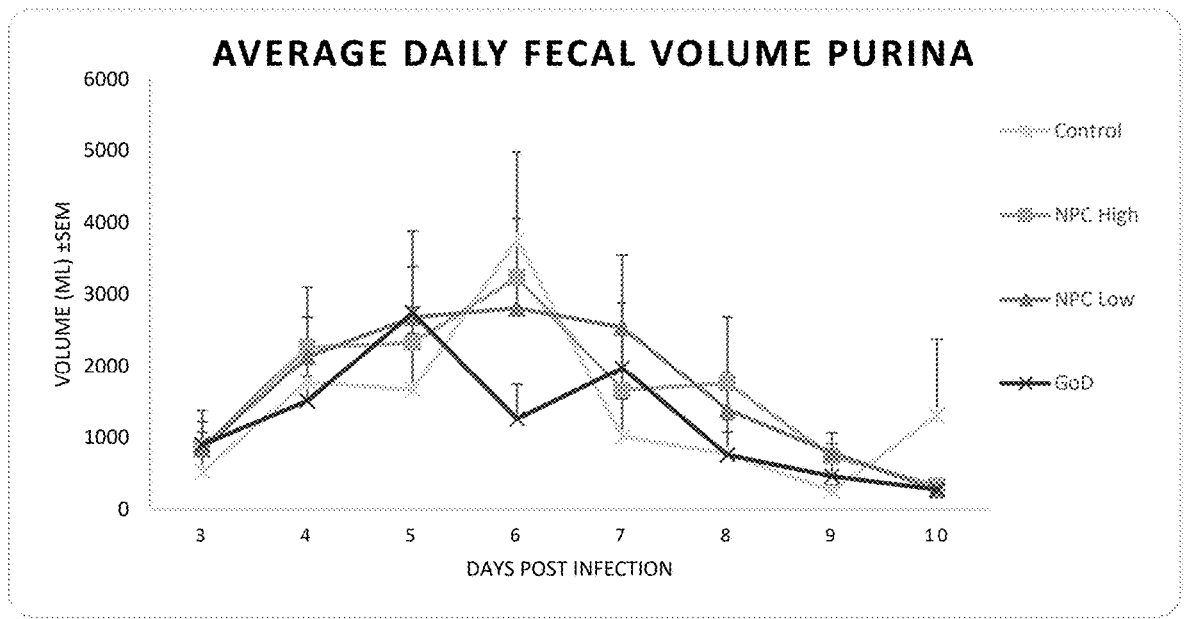
FIG. 6 is a line graph showing the average daily fecal volume of *C. parvum*-infected calves treated with 1000 mg NPC ("NPC High"), 500 mg NPC ("NPC Low"), or GoD BID or untreated.

The average daily fecal volume is largely a measure of diarrhea in which a greater volume indicates more diarrhea. Calves in all groups developed diarrhea. Only in the GOD treatment group on Day 6 PI was the volume statistically significantly less than the control group (p<0.05). FIG. 6. The total fecal volume for the duration of the trial was not significantly different between calves in the control and treatment groups (data not shown).

Figure 7:
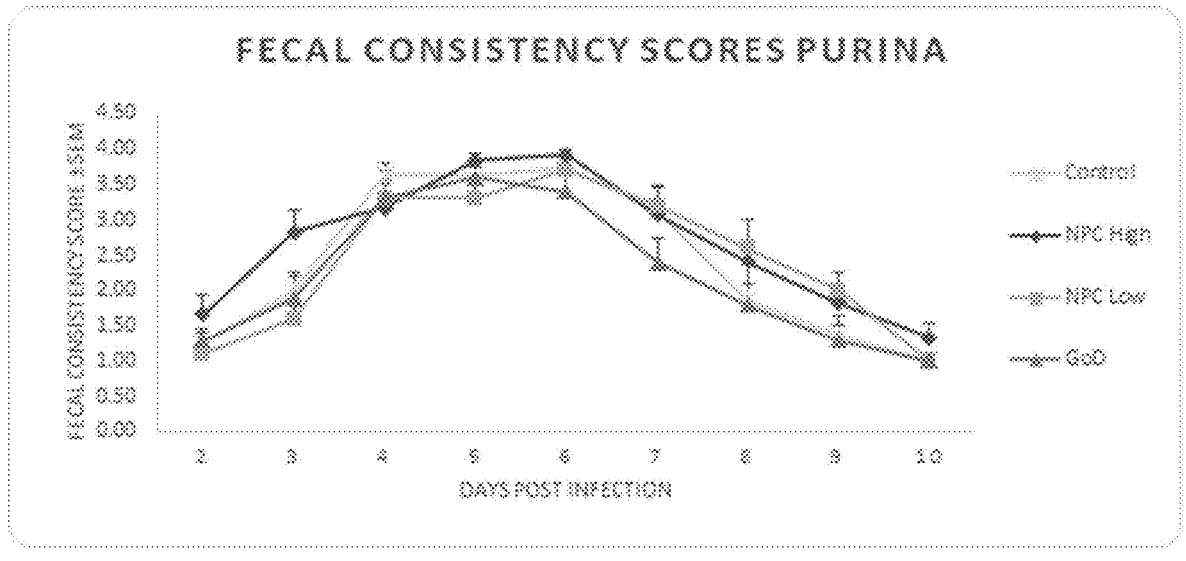
FIG. 7 is a line graph showing the average daily fecal consistency scores of *C. parvum*-infected calves treated with NPC High, NPC Low, or GoD BID or untreated.

Fecal consistency is a component of the clinical scoring rubric that grades feces on scale from 1 (normal, firm) to 4 (watery). Diarrhea or soft stools was persistent through most of the trial in both the control and treatment groups. As indicated in FIG. 7, calves in the control group exhibited substantial diarrhea from Day 3 PI through Day 9 PI. By Day 10 PI, the *C. parvum* infection had mostly cleared and the fecal consistency scores were similar to baseline (Day 2 PI). Overall, the treatment groups did not demonstrate an improvement in fecal consistency scores compared to the control group. Only on Day 7 PI did the GOD treatment group approach a statistically significant improvement in fecal consistency score compared to the control group.

In addition to fecal consistency, clinical evaluation scores assess each of stance, willingness to rise, appetite, attitude, and hydration on a scale of 1 (normal) to 4 (abnormal). Higher scores indicate a lower clinical evaluation or less healthy animal. No statistically significant differences were observed in clinical evaluation scores between control and treatment groups, whether analyzed daily or cumulatively over the course of the trial (data not shown).

Urine output is generally decreased in animals suffering from extreme diarrhea. No significant difference in daily or total urine volume was observed between control and treatment groups (data not shown).

Milk replacer intake for infected (control and treated) calves did not significantly differ from the intake expected for uninfected calves, based on the average weights of all calves in all trials, except for decreased intake on Day 4 PI, which generally coincided with the onset of diarrhea and inappetence (data not shown).

Example 4—Infectivity of Shed *Cryptosporidium* Oocysts

Oocysts were collected from feces of calves in the control and treatment groups of Example 3 on multiple days during the duration of the study. The oocysts were excysted and analyzed to ensure equal excystation rates between the four treatment groups. HCT-8 cells were infected, harvested, and processed as described in Example 1.

Figure 8:
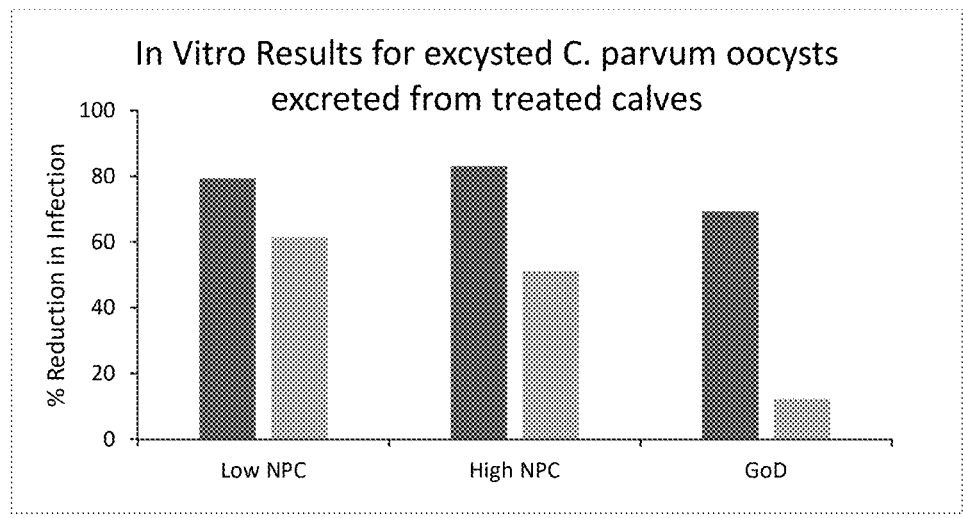
FIG. 8 is a bar graph showing the percent reduction in infection by *C. parvum* sporozoites excysted from oocysts shed by infected calves that had been treated with Low NPC, High NPC, or GoD compared to sporozoites excysted from oocysts shed by infected, untreated calves.

Results are shown in FIG. 8 with the first iteration shown in each left-hand bar of a pair (blue) and the second iteration shown in each right-hand bar (orange). All three treatment groups demonstrated a significant reduction in infection when compared to untreated control cells (p<0.05) in the first iteration of the assay although this was reduced for GOD in the second iteration. Calves treated with low- or high-dose sodium percarbonate or with glucose oxidase+dextrose shed oocysts that had a reduced ability to infect HCT-8 cells compared with oocysts shed from untreated (control) calves. Treating calves with a hydrogen peroxide-generating composition such as sodium percarbonate or glucose oxidase may reduce contamination of stall areas where calves are housed, may reduce environmental spread of cryptosporidiosis, and/or may improve overall outcomes for calves.

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates, or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. In some instances, the term "about" includes values up to and including 10% less than and 10% greater than the recited value.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the invention.

What is claimed is:

1. A method of feeding a calf susceptible to infection with *Cryptosporidium parvum*, the method comprising:
   providing a liquid feed to the calf, the liquid feed comprising:
      a hydrogen peroxide-generating composition admixed with the liquid feed, the composition including a source of hydrogen peroxide selected from sodium percarbonate and glucose oxidase with dextrose, wherein the source of hydrogen peroxide is provided at about 0.07 wt % to about 3.00 wt % of the liquid feed on a dry basis,
   wherein the *Cryptosporidium parvum* infection is prevented or reduced in the calf if the calf is exposed to *Cryptosporidium parvum*.

2. The method of claim 1, wherein in response to ingesting the composition, the calf gains weight.

3. The method of claim 1, wherein the liquid feed comprises whole milk, milk replacer, waste milk, or an electrolyte solution.

4. The method of claim 1, wherein the source of hydrogen peroxide is sodium percarbonate, and the sodium percarbonate is provided at 750 mg/head/day to 3000 mg/head/day.

5. The method of claim 1, wherein the source of hydrogen peroxide is sodium percarbonate, and the sodium percarbonate is provided at about 0.07 wt % to about 0.88 wt % on a dry basis.

6. The method of claim 1, wherein the source of hydrogen peroxide is glucose oxidase with dextrose, the glucose oxidase is provided at 140 mg/head/day to 250 mg/head/day when the glucose oxidase has a concentration of 10,000 U/g, and the dextrose is provided at 3.5 g/head/day to 10.0 g/head/day.

7. The method of claim 1, wherein the source of hydrogen peroxide is glucose oxidase with dextrose, the glucose oxidase is provided at about 0.01wt % to about 0.07 wt % when the glucose oxidase has a concentration of 10,000 U/g, and the dextrose is provided at about 0.31 wt % to about 2.94 wt % on a dry basis.

8. The method of claim 1, wherein the composition is first provided within 12 to 24 hours of birth, and then provided twice per day for 10 days.

9. The method of claim 1, wherein the source of hydrogen peroxide is encapsulated.

10. A method of feeding a livestock animal susceptible to contracting cryptosporidiosis, the method comprising:
   providing a feed to the livestock animal, the feed comprising:

a hydrogen peroxide-generating composition admixed with the feed, the composition including a source of hydrogen peroxide selected from sodium percarbonate and glucose oxidase with dextrose, wherein the source of hydrogen peroxide is provided at about 0.07 wt % to about 3.00 wt % of the feed on a dry basis, wherein contracting cryptosporidiosis is prevented or reduced in the animal if the animal is exposed to *Cryptosporidium* spp.

11. The method of claim 10, wherein the animal is a calf, lamb, goat kid, piglet, or foal.

12. The method of claim 10, wherein the animal is a calf and the *Cryptosporidium* spp. is *C. parvum*.

13. The method of claim 10, wherein the feed is a liquid feed and comprises whole milk, milk replacer, waste milk, or an electrolyte solution.

14. The method of claim 10, wherein the source of hydrogen peroxide is sodium percarbonate, and the sodium percarbonate is provided at 750 mg/head/day to 3000 mg/head/day.

15. The method of claim 10, wherein the source of hydrogen peroxide is sodium percarbonate, and the sodium percarbonate is provided at about 0.07 wt % to about 0.88 wt % on a dry basis.

16. The method of claim 10, wherein the source of hydrogen peroxide is glucose oxidase with dextrose, the glucose oxidase is provided at 140 mg/head/day to 250 mg/head/day when the glucose oxidase has a concentration of 10,000 U/g, and the dextrose is provided at 3.5 g/head/day to 10.0 g/head/day.

17. The method of claim 10, wherein the source of hydrogen peroxide is glucose oxidase with dextrose, the glucose oxidase is provided at about 0.01 wt % to about 0.07 wt % when the glucose oxidase has a concentration of 10,000 U/g, and the dextrose is provided at about 0.31 wt % to about 2.94 wt % on a dry basis.

18. The method of claim 10, wherein the composition is first provided within 12 to 24 hours of birth, and then provided twice per day for 10 days.

19. The method of claim 10, wherein the source of hydrogen peroxide is encapsulated.

* * * * *